United States Patent [19]

Baranski et al.

[11] Patent Number: 5,686,397
[45] Date of Patent: Nov. 11, 1997

[54] DITHIOCARBAMATE DERIVATIVES AND LUBRICANTS CONTAINING SAME

[75] Inventors: John R. Baranski, Southington, Conn.; Cyril A. Migdal, Pleasant Valley, N.Y.

[73] Assignee: Uniroyal Chemical Company, Inc., Middlebury, Conn.

[21] Appl. No.: 794,112

[22] Filed: Feb. 3, 1997

[51] Int. Cl.$^6$ .................... C10M 135/36; C07D 285/125
[52] U.S. Cl. ............................................. 508/274; 548/142
[58] Field of Search ............................. 508/274; 548/142

[56] References Cited

U.S. PATENT DOCUMENTS

| | | | |
|---|---|---|---|
| 2,685,588 | 8/1954 | Goshorn et al. | 508/274 |
| 2,690,999 | 10/1954 | Lowe et al. | 508/274 |
| 2,719,827 | 10/1955 | Lowe | 508/274 |
| 2,766,223 | 10/1956 | Goshorn et al. | 548/142 |
| 3,980,573 | 9/1976 | Okorodudu | 508/274 |
| 4,097,387 | 6/1978 | Caspari | 508/274 |
| 4,358,597 | 11/1982 | Fields | 548/142 |
| 4,410,703 | 10/1983 | Okorodudu | 548/142 |
| 4,678,592 | 7/1987 | Toukan | 252/25 |
| 4,740,454 | 4/1988 | Deguchi et al. | 548/142 |
| 4,904,403 | 2/1990 | Karol | 252/47.5 |
| 4,990,273 | 2/1991 | Croudace | 252/46.4 |
| 5,194,167 | 3/1993 | Hsu et al. | 252/34 |
| 5,414,090 | 5/1995 | Love et al. | 548/142 |

*Primary Examiner*—Jerry D. Johnson
*Attorney, Agent, or Firm*—Raymond D. Thompson

[57] ABSTRACT

A composition of matter is disclosed having the structure:

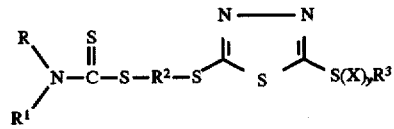

wherein R and $R^1$ are independently a member selected from the group consisting of alkyl, cycloalkyl, aryl, aralkyl, and alkaryl; $R^2$ is an alkylene moiety; $R^3$ is hydrogen, alkyl, alkenyl, aryl, alkaryl, aralkyl, or 2-hydroxyalkyl; X is sulfur; and y is 0 or 1. Lubricants and lubricant additives comprising the composition are also disclosed. The lubricants are preferably lubricating oils.

62 Claims, No Drawings

DITHIOCARBAMATE DERIVATIVES AND LUBRICANTS CONTAINING SAME

BACKGROUND OF THE INVENTION

1. Field of the Invention

This invention relates to lubricants. More particularly, the invention relates to a class of ashless, phosphorus-free, anti-fatigue, antiwear, extreme pressure, and friction modifying dithiocarbamate lubricant additives, preferably derived from a secondary amine, carbon disulfide, an allyl halide, and a 2-mercapto-1,3,4-thiadiazole.

2. Description of Related Art

In developing lubricating oils, there have been many attempts to provide additives that impart anti-fatigue, antiwear, and extreme pressure properties to the oils.

Zinc dialkyldithiophosphates (ZDDP) have been used in formulated oils as antiwear additives. However, zinc dialkyldithiophosphates give rise to ash, which contributes to particulate matter in automotive exhaust emissions. Regulatory agencies are seeking to reduce emissions of zinc into the environment. In addition, the phosphorus of these compounds is also suspected of limiting the service life of catalytic converters used on cars to reduce pollution. It is therefore important to limit the particulate matter and pollution formed during engine use for toxicological and environmental reasons, but it is also important to maintain the antiwear properties of the lubricating oil.

U.S. Pat. No. 4,358,597 discloses a thiocarbamate compound selected from the group consisting of 1,3,4-thiadiazole-2-thiol-5-monothiocarbamate, 1,3,4-thiadiazole-2,5-dithiocarbamate, 1,3,4-thiadiazole-2-thiol-5-mono(dithiocarbamate), and 1,3,4-thiadiazole-2,5-di(dithiocarbamate).

U.S. Pat. No. 4,410,703 discloses lubricants that are stabilized against wear and corrosion by adding an additive amount of a substituted thiadiazole derived from 2,5-dimercapto-1,3,4-thiadiazole and other moieties, such as an isocyanate moiety.

U.S. Pat. No. 4,678,592 discloses dimercapto thiadiazoles and cyanodithioimidocarbonate polymers and oil soluble lubricating additives thereof.

U.S. Pat. No. 4,904,403 discloses compounds derived from 2,5-dimercapto-1,3,4-thiadiazole and one or two moles of polyolefin having 5 to 400 carbon atoms. The five-position of the 2-mercapto-1,3,4-thiadiazole may be substituted by an alkylthio, a 2-hydroxyalkylthio, an amino, or a hydroxy group. The compounds are said to be effective dispersants, antiwear agents, and antioxidants when incorporated into lubricating compositions.

U.S. Pat. No. 4,990,273 discloses an extreme pressure, antiwear additive for lubricating compositions that is the reaction product of a 2,5-dimercapto-1,3,4-thiadiazole, an aldehyde, and a primary or secondary, aliphatic or alicyclic amine.

U.S. Pat. No. 5,194,167 discloses quaternary ammonium salts of mercaptothiadiazoles and related heterocyclic derivatives, which are said to be effective antioxidant and antiwear additives for lubricants and fuels.

U.S. Pat. No. 5,414,090 discloses an adduct of 2,5-dimercapto-1,3,4-thiadiazole, an epoxide, a formaldehyde, and 4,4'-isopropylidenediphenol, which is said to be useful as a lubricant additive.

One object of this invention is to provide novel dithiocarbamate compositions.

Another object of this invention is to provide a lubricant additive and lubricant composition containing such an additive, having improved dispersancy and being capable of withstanding the stresses imposed by modern internal combustion engines.

SUMMARY OF THE INVENTION

As stated above, the present invention is directed to lubricants, and more particularly to a class of ashless, phosphorus-free, anti-fatigue, antiwear, extreme pressure, and friction modifying dithiocarbamate lubricant additives. Preferably the additives are derived from a secondary amine, carbon disulfide, an allyl halide, and a 2-dimercapto-1,3,4-thiadiazole.

More particularly, the present invention relates to a composition of matter having the structure:

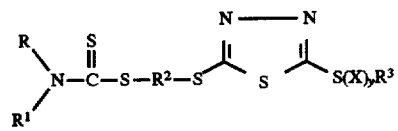

wherein R and $R^1$ are independently a member selected from the group consisting of alkyl, cycloalkyl, aryl, aralkyl, and alkaryl; $R^2$ is an alkylene moiety; $R^3$ is hydrogen, alkyl, alkenyl, aryl, alkaryl, aralkyl, or 2-hydroxyalkyl; X is sulfur; and y is 0 or 1.

DESCRIPTION OF THE PREFERRED EMBODIMENTS

The additives of this invention can be used as either partial or complete replacements for the zinc dialkyldithiophosphates currently used. The additives can also be used in combination with other additives typically found in motor oils, as well as with other ashless antiwear additives. The typical additives found in motor oils are dispersants, detergents, rust inhibitors, antioxidants, antifoamants, friction modifiers, viscosity index (VI) improvers, and pour point depressants.

The class of ashless and phosphorus-free, anti-fatigue, antiwear, extreme pressure, and friction modifying dithiocarbamate lubricant additives of the present invention are of the following structure:

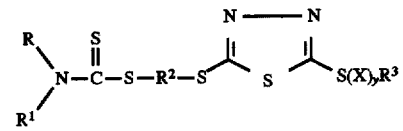

wherein R and $R^1$ are independently a member selected from the group consisting of alkyl, cycloalkyl, aryl, aralkyl, and alkaryl; $R^2$ is an alkylene moiety; $R^3$ is hydrogen, alkyl, alkenyl, aryl, alkaryl, aralkyl, or 2-hydroxyalkyl; X is sulfur; and y is 0 or 1.

Where R and/or $R^1$ are alkyl, these substituents preferably comprise from 1 to 24 carbon atoms, more preferably from 1 to 18 carbon atoms, and most preferably from 2 to 12 carbon atoms. Thus, the alkyl groups will be of the structure $C_nH_{2n+1}$, where n is an integer, preferably an integer in the range of 1 to 24. Where such alkyl groups comprise three or more carbon atoms, the groups can be either a straight chain or a branched chain. For example, R and/or $R^1$ can be methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosanyl, and the like, and isomers thereof.

Where R and/or $R^1$ are cycloalkyl, these substituents preferably comprise from 3 to 12 carbon atoms, more preferably from 4 to 8 carbon atoms. Thus, the cycloalkyl groups will be of the structure $C_nH_{2n-1}$, where n is an integer, preferably an integer in the range of 3 to 12. For example, R and/or $R^1$ can be cyclopropyl, cyclobutyl, cyclopentyl, cyclohexyl, cycloheptyl, cyclooctyl, and the like.

Where R and/or $R^1$ are aryl, aralkyl, or alkaryl, these substituents preferably comprise from 6 to 12 carbon atoms. Additionally, one or more of the ring carbon atoms can be replaced by an atom of a suitable alternative element, for example, nitrogen, oxygen, or sulfur. For example, R and/or $R^1$ can be a residue of benzene, toluene, xylene, indene, naphthalene, alpha-methylnaphthalene, beta-methylnaphthalene, diphenyl, acenaphthene, fluorene, phananthrene, anthracene, fluoranthene, pyrene, chrysene, naphthacene, pyridine, picoline, quinoline, isoquinoline, quinaldine, indole, acridine, carbazole, hemimellitene, pseudocumene, mesitylene, prehnitene, isodurene, durene, pentamethylbenzene, hexamethylbenzene, ethylbenzene, propylbenzene, cumene, butylbenzene, cymene, triethylbenzene, hexaethylbenzene, styrene, alpha-methylstyrene, allylbenzene, stilbene, diphenyl methane, triphenylmethane, tetraphenylmethane, terphenyl, quaterphenyl, 1,3,5-triphenylbenzene, and the like. Where R and/or $R^1$ is aryl, it is preferred that the substituent be a residue of benzene, i.e., a phenyl group. When R and $R^1$ are the same, it is more preferred that the substituents be alkyl, and most preferred that the substituents be tetradecyl.

Those skilled in the art readily appreciate that the above described moieties that can be employed as R and/or $R^1$ in the practice of the present invention can have various substituents attached thereto, provided that such substituents do not adversely affect the utility of the compositions as lubricant additives.

In the above structural formula, $R^2$ is an alkylene moiety, preferably an alkylene moiety of 1 to 12 carbon atoms, more preferably from 3 to 10 carbon atoms, and most preferably from 3 to 6 carbon atoms. Thus, the alkylene moiety has the structure $C_nH_{2n}$, where n is an integer, preferably an integer in the range of 1 to 12. Such alkylene moieties can be either a straight chain or a branched chain. For example, $R^2$ can be methylene (i.e., —CH$_2$—), ethylene (i.e., —CH$_2$CH$_2$—), propylene, butylene, pentylene, hexylene, heptylene, octylene, nonylene, decylene, undecylene, dodecylene, and the like, and isomers thereof.

The $R^3$ group of the above described structural formula can be hydrogen, alkyl, alkenyl, aryl, alkaryl, aralkyl, or 2-hydroxyalkyl.

Where $R^3$ is alkyl, it is preferably an alkyl of from 1 to 40 carbon atoms and can have either a straight chain or a branched chain, e.g. methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, triacontyl, pentatriacontyl, tetracontyl, and the like, and isomers and mixtures thereof.

Where $R^3$ is alkylene, it is preferably an alkylene of from 2 to 40 carbon atoms and can have either a straight chain or a branched chain, e.g. ethylene, propylene, butylene, pentylene, hexylene, heptylene, octylene, nonylene, decylene, undecylene, dodecylene, tridecylene, tetradecylene, pentadecylene, hexadecylene, heptadecylene, octadecylene, nonadecylene, eicosylene, heneicosylene, docosylene, tricosylene, tetracosylene, pentacosylene, triacontylene, pentatriacontylene, tetracontylene, and the like, and isomers and mixtures thereof.

Where $R^3$ is 2-hydroxyalkyl, it is preferably a 2-hydroxyalkyl of from 1 to 40 carbon atoms and can be either a straight chain or a branched chain, e.g. 2-hydroxymethyl, 2-hydroxyethyl, 2-hydroxypropyl, 2-hydroxybutyl, 2-hydroxypentyl, 2-hydroxyhexyl, 2-hydroxyheptyl, 2-hydroxyoctyl, 2-hydroxynonyl, 2-hydroxydecyl, 2-hydroxyundecyl, 2-hydroxydodecyl, 2-hydroxytridecyl, 2-hydroxytetradecyl, 2-hydroxypentadecyl, 2-hydroxyhexadecyl, 2-hydroxyheptadecyl, 2-hydroxyoctadecyl, 2-hydroxynonadecyl, 2-hydroxyeicosyl, 2-hydroxyheneicosyl, 2-hydroxydocosyl, 2-hydroxytricosyl, 2-hydroxytetracosyl, 2-hydroxypentacosyl, 2-hydroxytriacontyl, 2-hydroxypentatriacontyl, 2-hydroxytetracontyl, and the like, and isomers and mixtures thereof.

Where $R^3$ is aryl, aralkyl, or alkaryl, it preferably comprises from 6 to 12 carbon atoms. Additionally, one or more of the ring carbon atoms can be replaced by an atom of a suitable alternative element; for example, nitrogen, oxygen, or sulfur. For example, $R^1$ can be a residue of benzene, toluene, xylene, indene, naphthalene, alpha-methylnaphthalene, beta-methylnaphthalene, diphenyl, acenaphthene, fluorene, phananthrene, anthracene, fluoranthene, pyrene, chrysene, naphthacene, pyridine, picoline, quinoline, isoquinoline, quinaldine, indole, acridine, carbazole, hemimellitene, pseudocumene, mesitylene, prehnitene, isodurene, durene, pentamethylbenzene, hexamethylbenzene, ethylbenzene, propylbenzene, cumene, butylbenzene, cymene, triethylbenzene, hexaethylbenzene, styrene, alpha-methylstyrene, allylbenzene, stilbene, diphenyl methane, triphenylmethane, tetraphenylmethane, terphenyl, quaterphenyl, 1,3,5-triphenylbenzene, and the like. Where $R^3$ is aryl, it is preferred that it be a residue of benzene, i.e., a phenyl group.

Thiadiazoles useful in the practice of the present invention can be obtained commercially, for example, as the products sold under the trademarks VANCHEM® DMTD and VANLUBE® 829, both available from R. T. Vanderbilt Company, Inc. The chemical structure of VANCHEM® DMTD brand product is understood to be:

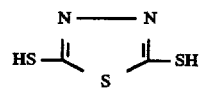

The chemical structure of VANLUBE® 829 brand product is understood to be:

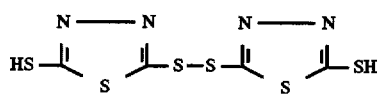

It is preferred that, in the above-described structural formula for the dithiocarbamate compounds of the invention, y be 0 and $R^3$ be hydrogen.

In a preferred embodiment, the dithiocarbamate derivatives of the present invention are prepared by the interreaction of a secondary amine, carbon disulfide, an allyl halide, and a 2,-mercapto-1,3,4-thiadiazole. The allyl halide can be, for example, allyl fluoride, allyl chloride, allyl bromide, allyl iodide, 3-chloro-1-butene, 3-chloro-2-methylpropene, 5-bromo-1-pentene, 8-bromo-1-octene, 6-bromo-1-hexene, or 4-bromo-1-butene. The preferred allyl halide is allyl chloride.

The thiadiazole is a 2-mercapto-1,3,4-thiadiazole characterized by the structural formula

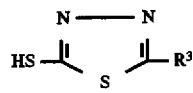

wherein $R^3$ can be hydrogen, alkyl, alkenyl, aryl, alkaryl, aralkyl, or 2-hydroxyalkyl as described above. The preferred thiadiazole is 2,5-dimercapto-1,3,4-thiadiazole, which can be purchased from R. T. Vanderbilt Company, Inc. under the trademark VANCHEM® DMTD.

The additives of the present invention are especially useful as components in lubricating oil compositions. The additives can be employed in a variety of oils of lubricating viscosity including natural and synthetic lubricating oils and mixtures thereof. The additives can be employed in crankcase lubricating oils for spark-ignited and compression-ignited internal combustion engines. The compositions can also be used in gas engine lubricants, turbine lubricants, automatic transmission fluids, gear lubricants, metalworking lubricants, hydraulic fluids, and other lubricating oil and grease compositions. The additive can also be used in motor fuel compositions.

In general, the lubricant compositions of the invention contain the additives in a concentration ranging from about 0.1 to about 30 weight percent. A concentration range for the additives ranging from about 0.5 to about 15 weight percent based on the total weight of the oil composition is preferred, with a still more preferred concentration range being from about 1.0 to about 7.5 weight percent.

Oil concentrates of the additives can contain from about 1.0 to about 50 weight percent of the additive reaction product in a carrier or diluent oil of lubricating oil viscosity.

The additives of the present invention can be employed in lubricant compositions together with conventional lubricant additives. As mentioned above, the typical additives found in lubricating oil compositions are dispersants, detergents, rust inhibitors, antioxidants, antifoamants, friction modifiers, VI improvers, and pour point depressants.

The advantages and the important features of the present invention will be more apparent from the following examples.

EXAMPLE 1

A two-liter bottom-out resin kettle reactor equipped with an overhead stirrer, a thermocouple, a pressure-equalizing addition funnel, a Dean-Stark trap, and a condenser was charged with 0.750 mol of di(tetradecyl)amine, 500 milliliters of reagent 2-propanol, and 0.750 mol of NaOH. A quantity of 0.798 mol of carbon disulfide was charged to the addition funnel. The reactor was heated to 50° C. Once a homogeneous solution was observed, the reaction temperature was lowered to 38° C. Carbon disulfide was added over one-half hour. The reaction temperature was lowered from 38° C. to 20° C. over the course of the carbon disulfide addition. The product was post-reacted at 20° to 25° C. for one hour. A quantity of 0.798 mol of allyl chloride was added to the reactor, containing the product of step 1, over a half-hour period with the reaction temperature being maintained at 25° C. The product was post-reacted at 28° C. for one-half hour, then raised to 45° C., and held at that temperature for one hour. The product of step 2 was washed three times with 800 milliliters of hot (70° C.) deionized water. A quantity of 500 milliliters of reagent butyl acetate was added to the reactor. Then, 0.746 mol of 2,5-dimercapto-1,3,4-thiadiazole was added to the reactor. The system was heated to reflux. The residual water was removed using the Dean-Stark trap. Reflux was maintained for seven hours. The solvent was removed using a rotary evaporator. The product was pressure-filtered through a one-micron filter to remove any residual solids.

A quantity of 465 grams of a dark reddish-brown liquid having a moderate viscosity was recovered in 92 percent yield. The product was characterized by $H^1 NMR$ and IR.

EXAMPLE 2

The antiwear properties of the reaction product of this invention in a fully formulated lubricating oil were determined in the "Four-Ball Wear Test," described below, under the ASTM D 4172 test conditions. The fully formulated lubricating oils tested in this example also contained 1.0 weight percent cumene hydroperoxide to simulate the condition within a running engine. The additives were tested for effectiveness in two motor oil formulations, as described in Table 2, and compared to identical formulations with and without any zinc dialkyldithiophosphate. In Table 1 the numerical value of the test results (Average Wear Scar Diameter "mm") decreases with an increase in effectiveness. In many instances, antiwear additives are effective in lubricating oil containing no other additives. However, in fully formulated oils such additives may not perform well.

Four-Ball Wear Test

I. Purpose of Tests

The "Four-Ball Wear Test" evaluates the antiwear performance of oil and grease formulations and transportation fuels, such as diesel.

II. Apparatus

A Four-Ball Wear Test machine is used to perform this evaluation. Four balls are arranged in an equilateral tetrahedron. The lower three balls are clamped securely in a test cup filled with lubricant and the upper ball is held by a chuck that is motor-driven. The upper ball rotates against the fixed lower balls. Load is applied in an upward direction through a weight/lever arm system. Loading is through a continuously variable pneumatic loading system. Heaters allow operation at elevated oil temperatures.

The testing of this example was done on a Falex Variable Drive Four-Ball Wear Test Machine.

III. Test Procedures

The three stationary steel balls are immersed in 10 milliliters of formulated oil to be tested, and the fourth steel ball is rotated on top of the three stationary balls in "point-to-point contact." The machine is operated for one hour at 75° C. with a load of 40 kilograms and a rotational speed of 1,200 revolutions per minute.

TABLE 1

Four Ball Wear Results

| Compound | Formulation | Wear Scar Diameter "mm" |
|---|---|---|
| 1-{propyl-2-(S-{mercapto-thioliazoylthio})}-N,N-di(tetradecyl)- | A | 0.51 |

TABLE 1-continued

Four Ball Wear Results

| Compound | Formulation | Wear Scar Diameter "mm" |
|---|---|---|
| dithiocarbamate | | |
| No antiwear additive | A | 0.93 |
| Zinc dialkyldithiophosphate | A | 0.46 |
| 1-{propyl-2-(S-{mercapto-thioliazoylthio})}-N,N-di(tetradecyl) dithiocarbamate | B | 0.57 |
| No antiwear additive | B | 0.98 |
| Zinc dialkyldithiophosphate | B | 0.53 |

TABLE 2

SAE 10W-30 Motor Oil Formulations

| Formulation A | wt. % | Formulation B | wt. % |
|---|---|---|---|
| Solvent Neutral 100 | 22.8 | Solvent Neutral 100 | 22.8 |
| Solvent Neutral 150 | 60.0 | Solvent Neutral 150 | 60.0 |
| Succinimide Dispersant | 7.5 | Succinimide Dispersant | 7.5 |
| Overbased Calcium Phenate Detergent | 2.0 | Overbased Calcium Sulfonate Detergent | 2.0 |
| Neutral Calcium Sulfonate Detergent | 0.5 | Neutral Calcium Sulfonate Detergent | 0.5 |
| Antioxidant | 0.5 | Antioxidant | 0.5 |
| Rust Inhibitor | 0.1 | Rust Inhibitor | 0.1 |
| Pour Point Depressant | 0.1 | Pour Point Depressant | 0.1 |
| OCP VI Improver | 5.5 | OCP VI Improver | 5.5 |
| Antiwear Additive[1] | 1.0 | Antiwear Additive | 1.0 |

[1]In the case of "no antiwear additive" in Table 1, the product sold under the trademark Solvent Neutral 150 is used in place of an additive at 1.0 weight percent.

The invention has been described in detail with particular reference to preferred embodiments thereof, but it will be understood that variations and modifications can be effected within the spirit and scope of the invention.

What is claimed is:

1. A composition of matter having the structure:

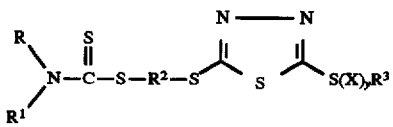

wherein R and $R^1$ are independently a member selected from the group consisting of alkyl, cycloalkyl, aryl, aralkyl, and alkaryl; $R^2$ is an alkylene moiety; $R^3$ is hydrogen, alkyl, alkenyl, aryl, alkaryl, aralkyl, or 2-hydroxyalkyl; X is sulfur; and y is 0 or 1.

2. The composition of claim 1 wherein R is alkyl.
3. The composition of claim 2 wherein $R^1$ is alkyl.
4. The composition of claim 3 wherein $R^2$ is a lower alkylene group of three to ten carbon atoms.
5. The composition of claim 4 wherein y is 0 and $R^3$ is hydrogen.
6. The composition of claim 3 wherein $R^2$ is isopropylene.
7. The composition of claim 6 wherein y is 0 and $R^3$ is hydrogen.
8. The composition of claim 3 wherein y is 0 and $R^3$ is hydrogen.
9. The composition of claim 1 wherein R is tetradecyl.
10. The composition of claim 9 wherein $R^1$ is tetradecyl.
11. The composition of claim 10 wherein $R^2$ is a lower alkylene group of three to ten carbon atoms.
12. The composition of claim 11 wherein y is 0 and $R^3$ is hydrogen.
13. The composition of claim 10 wherein $R^2$ is isopropylene.
14. The composition of claim 10 wherein y is 0 and $R^3$ is hydrogen.
15. The composition of claim 1 wherein $R^2$ is a lower alkylene group of one to twelve carbon atoms.
16. The composition of claim 15 wherein y is 0 and $R^3$ is hydrogen.
17. The composition of claim 1 wherein $R^2$ is isopropylene.
18. The composition of claim 17 wherein y is 0 and $R^3$ is hydrogen.
19. The composition of claim 1 wherein y is 0 and $R^3$ is hydrogen.
20. 1{propyl-2-(S-{mercaptothioliazoylthio})}-N,N-di(tetradecyl)dithiocarbamate.
21. A lubricant additive comprising a composition of matter having the structure:

wherein R and $R^1$ are independently a member selected from the group consisting of alkyl, cycloalkyl, aryl, aralkyl, and alkaryl; $R^2$ is an alkylene moiety; $R^3$ is hydrogen, alkyl, alkenyl, aryl, alkaryl, aralkyl, or 2-hydroxyalkyl; X is sulfur; and y is 0 or 1.

22. The additive of claim 21 wherein the additive is a lubricating oil additive.
23. The additive of claim 21 wherein R is alkyl.
24. The additive of claim 23 wherein $R^1$ is alkyl.
25. The additive of claim 24 wherein $R^2$ is isopropylene.
26. The additive of claim 25 wherein y is 0 and $R^3$ is hydrogen.
27. The additive of claim 24 wherein $R^2$ is a lower alkylene group of three to ten carbon atoms.
28. The additive of claim 27 wherein y is 0 and $R^3$ is hydrogen.
29. The additive of claim 24 wherein y is 0 and $R^3$ is hydrogen.
30. The additive of claim 21 wherein R is tetradecyl.
31. The additive of claim 30 wherein $R^1$ is tetradecyl.
32. The additive of claim 31 wherein $R^2$ is a lower alkylene group of three to ten carbon atoms.
33. The additive of claim 32 wherein y is 0 and $R^3$ is hydrogen.
34. The additive of claim 31 wherein $R^2$ is isopropylene.
35. The additive of claim 31 wherein y is 0 and $R^3$ is hydrogen.
36. The additive of claim 21 wherein $R^2$ is a lower alkylene group of three to ten carbon atoms.
37. The additive of claim 36 wherein y is 0 and $R^3$ is hydrogen.
38. The additive of claim 21 wherein $R^2$ is isopropylene.
39. The additive of claim 38 wherein y is 0 and $R^3$ is hydrogen.
40. The additive of claim 21 wherein y is 0 and $R^3$ is hydrogen.
41. The additive of claim 21 wherein said additive is 1{propyl-2-(S-{mercaptothioliazoylthio})}-N,N-di(tetradecyl)dithiocarbamate.

42. A lubricant comprising a lubricant additive comprising a composition of matter having the structure:

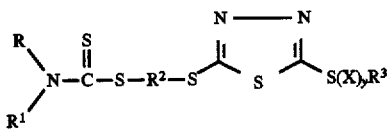

wherein R and $R^1$ are independently a member selected from the group consisting of alkyl, cycloalkyl, aryl, aralkyl, and alkaryl; $R^2$ is an alkylene moiety; $R^3$ is hydrogen, alkyl, alkenyl, aryl, alkaryl, aralkyl, or 2-hydroxyalkyl; X is sulfur; and y is 0 or 1.

43. The lubricant of claim 42 wherein said lubricant is a lubricating oil.
44. The lubricant of claim 42 wherein R is alkyl.
45. The lubricant of claim 44 wherein $R^1$ is alkyl.
46. The lubricant of claim 45 wherein $R^2$ is a lower alkylene group of three to ten carbon atoms.
47. The lubricant of claim 46 wherein y is 0 and $R^3$ is hydrogen.
48. The lubricant of claim 45 wherein $R^2$ is isopropylene.
49. The lubricant of claim 48 wherein y is 0 and $R^3$ is hydrogen.
50. The lubricant of claim 45 wherein y is 0 and $R^3$ is hydrogen.
51. The lubricant of claim 42 wherein R is tetradecyl.
52. The lubricant of claim 51 wherein $R^1$ is tetradecyl.
53. The lubricant of claim 52 wherein $R^2$ is a lower alkylene group of three to ten carbon atoms.
54. The lubricant of claim 53 wherein y is 0 and $R^3$ is hydrogen.
55. The lubricant of claim 52 wherein $R^2$ is isopropylene.
56. The lubricant of claim 52 wherein y is 0 and $R^3$ is hydrogen.
57. The lubricant of claim 42 wherein $R^2$ is a lower alkylene group of three to ten carbon atoms.
58. The lubricant of claim 57 wherein y is 0 and $R^3$ is hydrogen.
59. The lubricant of claim 42 wherein $R^2$ is isopropylene.
60. The lubricant of claim 59 wherein y is 0 and $R^3$ is hydrogen.
61. The lubricant of claim 42 wherein y is 0 and $R^3$ is hydrogen.
62. The lubricant of claim 42 wherein the additive is 1{propyl-2-(S-{mercaptothioliazoylthio})}-N,N-di(tetradecyl)dithiocarbamate.

* * * * *